United States Patent [19]

Lindsay et al.

[11] Patent Number: 5,244,568
[45] Date of Patent: Sep. 14, 1993

[54] AUTOMATED HEMODIALYSIS CHEMICAL TREATMENT SYSTEM WITH CONTROL VALVE AND PROPORTIONING PUMPS

[75] Inventors: Edward R. Lindsay, Dunedin; Robert C. Kusmierczyk, Pinellas Park, both of Fla.

[73] Assignee: Baxter International Inc., Deerfield, Ill.

[21] Appl. No.: 795,909

[22] Filed: Nov. 15, 1991

[51] Int. Cl.$^5$ .............................................. B01D 65/02
[52] U.S. Cl. ...................................... 210/87; 210/91; 210/97; 210/321.69; 210/321.71; 210/647
[58] Field of Search ................... 137/909; 210/91, 962, 210/321.69, 321.71, 646, 929, 85, 647, 87; 285/1

[56] References Cited

U.S. PATENT DOCUMENTS

| | | | |
|---|---|---|---|
| 3,992,301 | 11/1976 | Shippey et al. | 210/321.69 |
| 4,331,540 | 5/1982 | Witsoe | 210/321.69 |
| 4,399,036 | 8/1983 | Babb et al. | 210/321.71 |
| 4,601,830 | 7/1986 | Chen | 210/647 |
| 4,789,467 | 12/1988 | Lindsay et al. | 210/321.71 |
| 4,828,693 | 5/1989 | Lindsay et al. | 210/321.71 |
| 4,857,181 | 8/1989 | Shouldice et al. | 210/321.69 |

Primary Examiner—Joseph W. Drodge
Attorney, Agent, or Firm—Charles R. 300101son; John T. Winburn

[57] ABSTRACT

An improved chemical treatment system for hemodialysis machines, which includes a first three way valve which has a normally open position in the dialysis and rinsing modes of the hemodialysis machine. The valve in the normally open position couples a source of water through the valve to the bicarbonate pump for rinsing purposes before and after dialysis and the chemical treatment modes of the hemodialysis machine. In the chemical treatment mode of the hemodialysis machine the valve is switched to couple a source of treatment chemical through the valve to the bicarbonate pump. The chemical treatment system includes a second valve, which if in the normally open position, then only the bicarbonate portion and associated downstream portions will be chemically treated. In the closed position, the chemical will be switched to also flow through the whole hemodialysis machine from the water inlet to provide for a half or total system chemical treatment cycle. A vent valve coupled to the first valve can be included to further ensure that chemicals are not inadvertently entered into the hemodialysis machine.

54 Claims, 4 Drawing Sheets

AUTOMATED HEMODIALYSIS CHEMICAL TREATMENT SYSTEM WITH CONTROL VALVE AND PROPORTIONING PUMPS

FIELD OF THE INVENTION

The present invention relates generally to cleaning of hemodialysis machines, and more particularly is directed to an improved automated chemical treatment system for hemodialysis machines.

BACKGROUND OF THE INVENTION

Hemodialysis machines are utilized by persons having insufficient or inoperative kidney functions. The machines may be used at a health facility or in the patient's home. The machine attaches to the patient through an extracorporeal circuit of blood tubing to a dialyzer having a pair of chambers separated by a thin semi-permeable membrane. The patient's blood is circulated through one of the chambers. The hemodialysis machine maintains a constant flow of a dialysate through the second chamber. Excess water from the blood is removed by ultrafiltration through the membrane and carried out by the dialysate to a drain.

A typical hemodialysis machine provides a pair of hoses which connect to the dialyzer and include a source of incoming water, a heat exchanger and heater for bringing the water to a required temperature, a source of a dialysate concentrate or concentrates which are introduced into the water in a predetermined concentration and necessary pumps, pressure regulators, a deaerator, flow controllers and regulators. In an acetate dialysis system, only one concentrate is utilized, while in the more common bicarbonate dialysis systems, two concentrates, acidified and bicarbonate are utilized.

After use, the hoses are removed from the dialyzer and connected to a bypass which couples the two hoses together. It is then necessary to clean the dialysate from the machine and the various tubes, hoses and other elements and to clean/disinfect/sterilize the various lines and parts of the machine.

Numerous chemicals are utilized for cleaning, disinfecting and sterilizing hemodialysis machines. The cleaning, disinfecting, sterilizing treatments will generally be designated as chemical treatments hereinafter. Some of the more common chemicals are bleach, formaldehyde, vinegar, Actril and Renalin. (Actril and Renalin are registered trademarks of Renal systems, a Division of Minntech Corporation of Minneapolis, Minn.). Before any of the chemicals are introduced into the hemodialysis machine, the hemodialysis machine must be pre-rinsed. Next, the selected chemical is proportioned with water and either cycled to drain or allowed to remain in the hemodialysis machine for a desired dwell period. Dwell periods can be a few minutes, overnight or several days. Following any chemical treatment, the hemodialysis machine is again rinsed to ensure removal of residual chemicals. The operator generally will perform a manual chemical check to confirm that all chemicals have been removed.

These chemicals are hazardous to the patient and the operator must be extremely careful not to inadvertently dialyze with any of these chemicals remaining in the system. Although some apparatus may have safety devices which require certain conductivity of the dialysate, there are occasions in which improper concentrations have been utilized and serious injury or death to a patient has occurred. Therefore, safety is of utmost concern.

An improved disinfection system is disclosed in U.S. Pat. No. 4,789,467, assigned to the present assignee. This disinfection system discloses an improved cleaning system with enhanced safety features with vent and check valves utilized to ensure that disinfectant is not drawn into the hemodialysis machines.

SUMMARY OF THE INVENTION

The present invention is directed to an improved chemical treatment system for hemodialysis machines. The chemical treatment system includes a first three way valve which is in a normally open position in the dialysis and rinsing modes of the hemodialysis machine. The valve in the normally open position couples a source of water through the first valve to the bicarbonate pump for rinsing purposes before and after dialysis and chemical treatment modes of the hemodialysis machine. In the dialysis mode the first valve remains in the normally open position with the chemical intake port closed. This provides a safety measure against inadvertent chemical exposure. In the chemical treatment mode of the hemodialysis machine the valve is switched to couple a chemical source through the valve to the bicarbonate pump. The chemical treatment system includes a second valve which can be the same type as the first three way valve. If the second valve is in the normally open position the fluid path downstream of the bicarbonate pump will be chemically treated. If the second valve is in the energized position, the chemical will be switched to the water inlet of the hemodialysis machine. In this position most of the hemodialysis fluid path is exposed to the chemical providing for a total chemical treatment. Thus the chemical treatment system provides for a half or total system chemical treatment cycle.

The chemical treatment system preferably includes a third valve that provides an air vent and is coupled to the first valve to further ensure that chemical is not inadvertently directed into the hemodialysis machines. In the normally open position, the vent valve opens the chemical inlet to air. The vent valve has to be positively energized to close, which prevents air from being drawn into the hemodialysis machine. The suction of the bicarbonate pump then is allowed to draw chemical from the source coupled to the chemical port.

These and other features and advantages of the invention will be more readily apparent upon reading the following description of a preferred exemplified embodiment of the invention and upon reference to the accompanying drawings wherein:

While the invention will be described and disclosed in connection with certain preferred embodiments and procedures, it is not intended to limit the invention to those specific embodiments. Rather it is intended to cover all such alternative embodiments and modifications as fall within the spirit and scope of the invention.

DETAILED DESCRIPTION OF THE PREFERRED EMBODIMENTS

Figure 1:
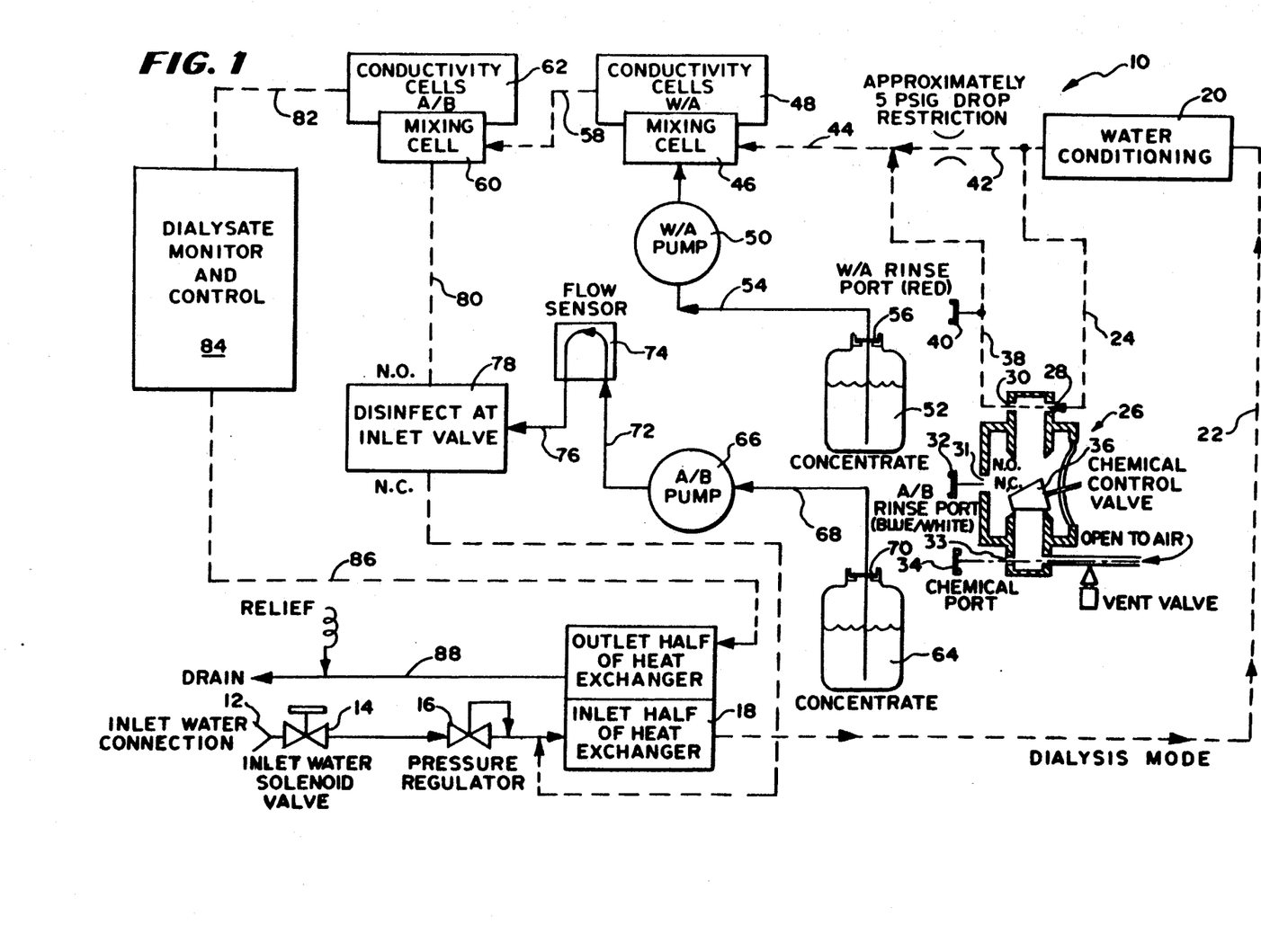
FIG. 1 is a schematic diagram of one embodiment of the chemical treatment system of the present invention in a dialysis mode.

Referring to FIG. 1, a hemodialysis machine into which the present invention can be provided is designated generally by the reference numeral 10. The hemodialysis machine 10 is configured in a dialysis mode in FIG. 1. The hemodialysis machine 10 is connected to a source of pre-treated water (not illustrated) through an inlet connection 12. The water preferably is fed through an inlet water solenoid valve 14 and a pressure regulator 16 to the inlet side of a heat exchanger 18.

The heat exchanger 18 provides heat from the waste fluid utilized in the dialysis operation to preheat the input water. The water then is fed to a water conditioning unit or units 20 via a line 22. The water conditioning unit 20 can include further heating of the water, deaeration of the water and monitoring of the water pressure, water pressure regulation and a water pump since the hemodialysis machine 10 will be deactivated if there is not a sufficient volume of water for a viable dialysis operation.

From the water conditioning unit 20 the water is separated into two streams. A first stream is fed via a line 24 to a chemical control valve 26. The chemical control valve 26 is one of the main elements forming the chemical treatment system of the present invention. The chemical control valve 26 is illustrated in its normal non-energized state. The chemical control valve 26 includes an inlet 28 which is always coupled to a first outlet 30. The chemical control valve 26 also includes a second outlet 31 which connects to a female connector 32 which forms an acetate/bicarbonate (A/B) rinse port. The port 32 is closed during the dialysis mode by an internal spring activated valve (not illustrated). The chemical control valve 26 also includes a chemical inlet 33, which connects to a male connector 34 which forms a chemical port, which is closed by a valve member 36 in the dialysis mode. In addition, the port 34 is closed by an internal spring activated valve (not illustrated) like the port 32.

The water is fed continuously through the chemical control valve 26 via inlet 28 and the outlet 30 to a line 38. A water/acid (W/A) rinse port is formed by another female connector 40 connected to the line 38, and also is closed during the dialysis mode like the port A/B 32.

The second water stream is fed from the water conditioning unit 20 through a restrictor 42 to a line 44, which also is fed the first stream of water from the line 38. The main flow of water is through the restrictor 42, but the flow through the lines 24 and 38 prevent stagnation in these elements. The water from the line 44 is fed into a mixing cell 46, which can form part of or be coupled to a conductivity cell or cells 48. The conductivity cell or cells 48 is utilized to sense the conductivity of the solution which then preferably is utilized in a servo-loop to adjust the conductivity to a desired level by adjusting the output of a W/A pump 50.

The conductivity preferably is controlled as described in copending application U.S. Ser. No. 07/795,908, entitled *Hemodialysis Conductivity Servoproportioning System*, filed concurrently herewith on Nov. 15, 1991, now U.S. Ser. No. 795,908, which is incorporated herein by reference. The W/A pump 50 also preferably is the type of pump disclosed in copending U.S. Ser. No. 07/685,584 now U.S. Pat. No. 5,158,441 issued Oct. 27, 1992, filed Apr. 15, 1991, entitled *Proportioning Device*, which also is incorporated herein by reference.

The W/A pump 50 is connected to a source of acidified concentrate 52 via a line 54 and a connector 56. The W/A pump 50 is driven to provide the proper amount of the concentrate desired for the dialysis operation. The water/acidified mixture is fed from the conductivity cell or cells 48 via a line 58 to a mixing cell 60, again forming a part of or coupled to an A/B conductivity cell or cells 62.

The bicarbonate component is provided from a bicarbonate concentrate source 64 which is fed by an A/B pump 66 to the mixing cell 60. The pump 66 preferably is the same type as the pump 50, which provides a very controlled output as will be described in more detail hereinafter.

The concentrate is fed via a line 68 through a connector 70, through the pump 66 and a line 72 to a flow sensor 74. The flow sensor 74 can be any type of sensor which is sensitive enough to accurately sense the presence of low and pulsatile flow rates. One particular flow sensor 74 is formed by mounting a very thin disc loosely on a central pivot pin. The fluid space between the disc and the pin provides lubricant for the flow sensor 74. The disc includes radical paddles spaced around the disc perimeter. The concentrate fluid is directed as a high velocity jet tangentially to the disc and at the paddles, which causes the disc to rotate. A light weight structure enables the disc to rotate at the required low and pulsatile flow rates.

An optical shutter is formed in the disc by an opening extending radially to the disc perimeter to prevent trapping air bubbles. An optical sensor monitors the disc rotation through a transparent housing or housing portion and through the shutter opening as it rotates past the optical sensor. A larger exit line is formed above the fluid inlet to facilitate air bubble removal. The light, open disc and paddle structure allows all air bubbles to flow through the flow sensor 74 without causing significant surface tension resistance.

The fluid then is fed via a line 76 through a valve 78, which can be the same type of valve as the chemical control valve 26, and via a line 80 to the mixing cell 60. The conductivity cell or cells 62 is utilized to control the pump 66 to provide the proper amount of the A/B concentrate.

The combined fluid, typically nominally including thirty-four (34) parts water, one (1) part acidified concentrate from the source 52 and 1.83 parts bicarbonate concentrate from the source 64, then is fed via a line 82 to a dialysate monitor and control unit and or units 84. The unit 84 includes the conventional dialysate components including the dialyzer and related sensing and monitoring components. The used waste fluid is fed via a line 86 through the outlet half of the heat exchanger 18 to a drain line 88.

Figure 2:
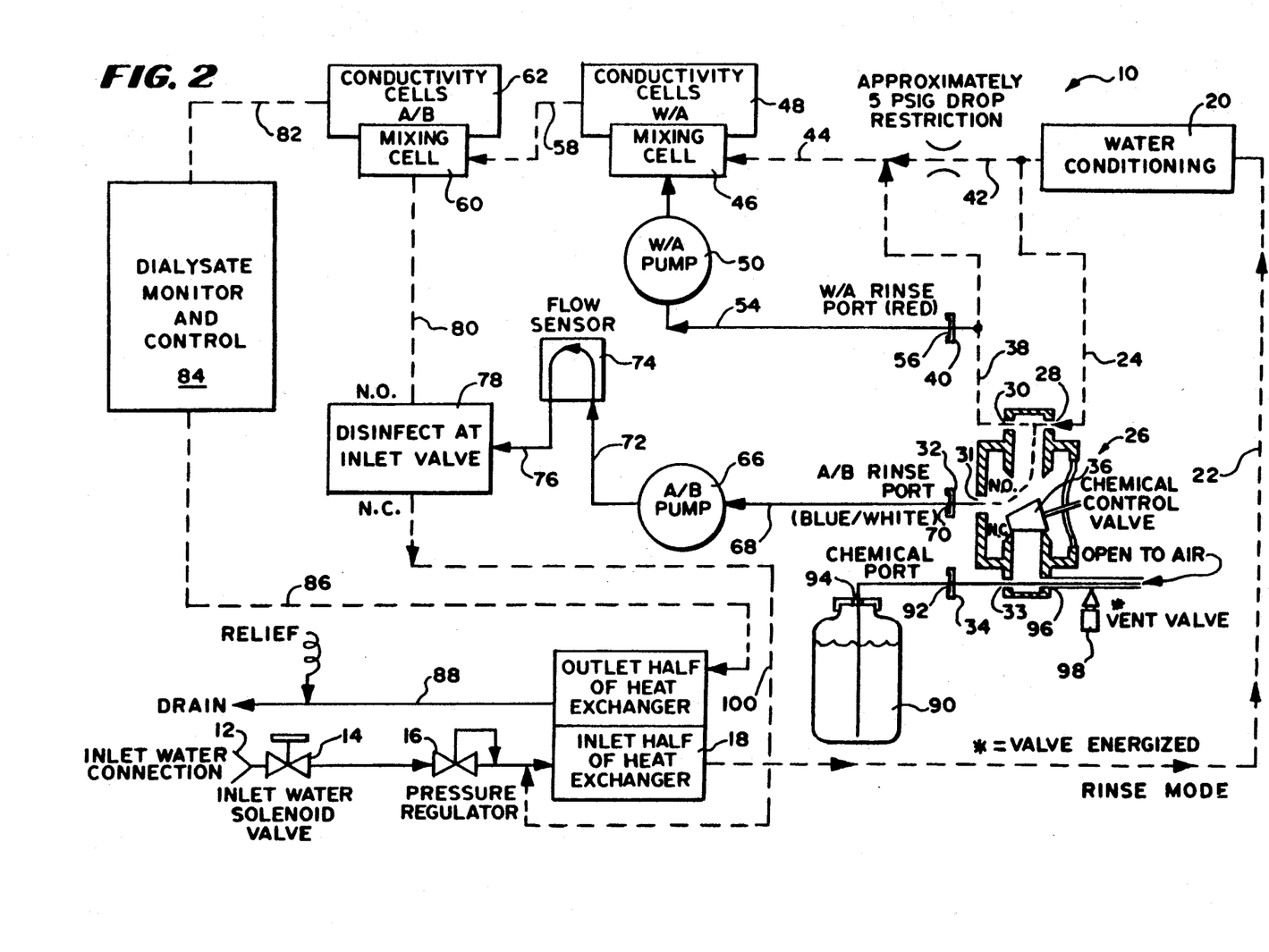
FIG. 2 is a schematic diagram of the embodiment of the chemical treatment system of FIG. 1 in a rinse mode.

When the dialysis mode is completed, the hemodialysis machine must be chemically treated. The first step is a rinse mode illustrated in FIG. 2. A first pre-rinse step is required to remove residual dialysate and concentrates to prevent any potential adverse chemical reactions with the treatment chemicals. The operation is similar to the dialysis mode, except that the concentrate sources 52 and 64 are disconnected and the lines 54 and 68 are connected to the ports 40 and 32 via the connectors 56 and 70. The connections 56 and 70 to the ports 40 and 32 open these ports and the pumps 50 and 66 then meter water through their respective components to rinse the hemodialysis machine 10.

Figure 3:
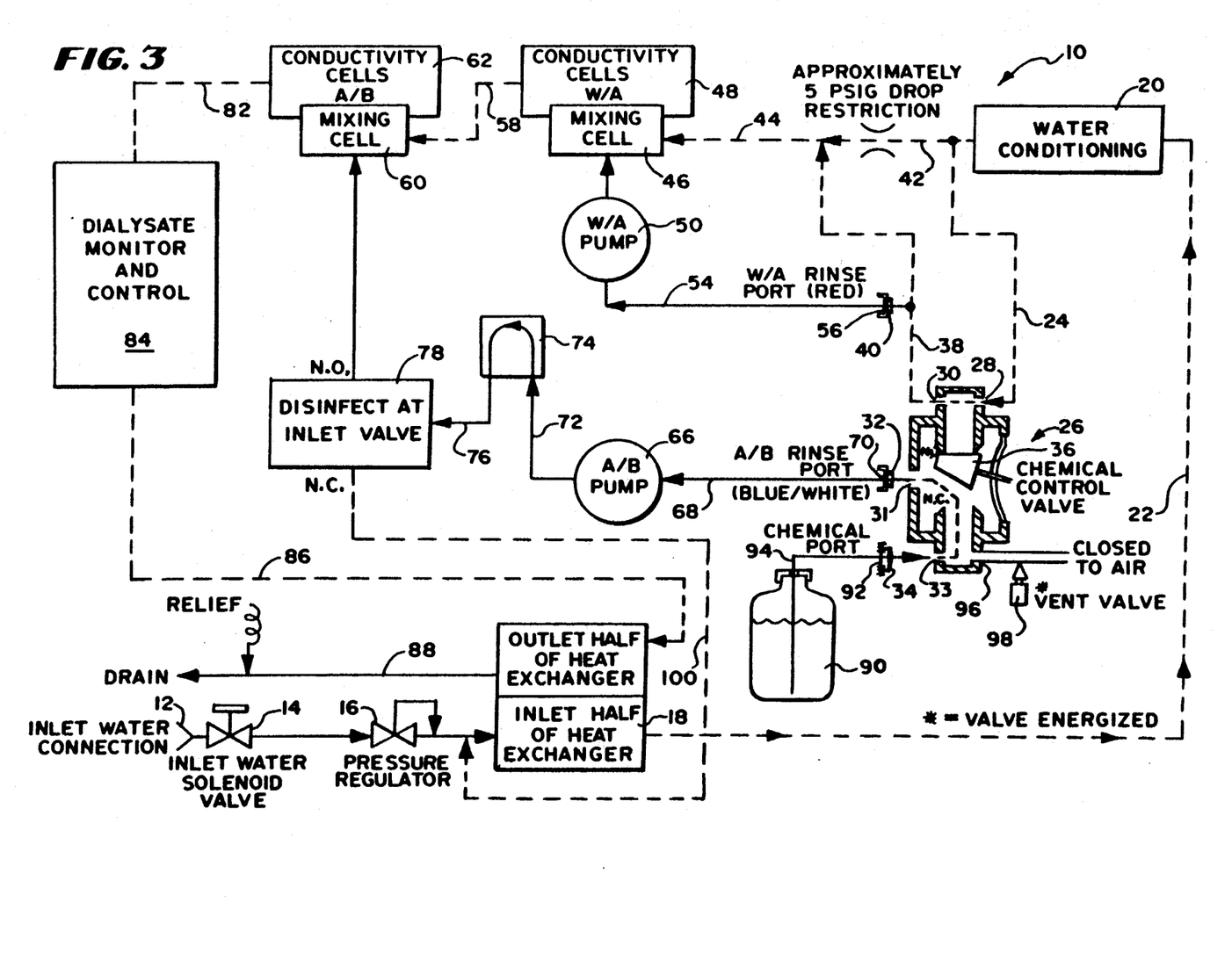
FIG. 3 is a schematic diagram of the embodiment of the chemical treatment system of FIG. 1 in a chemical treatment mode.

The next step in the chemical treatment mode is to supply a treatment chemical to the hemodialysis machine 10 as best illustrated in FIG. 3. The chemical treatment system connections are similar to the rinse mode with the exception that a chemical source 90 now is coupled to the port 34 via a connector 92 and a line 94.

The chemical control valve 26 also includes an inlet 96, which is opened or closed to air by a vent valve 98. The vent valve 98 has a normally open position, as illustrated in FIG. 1. In this position, inadvertent pumping of the chemical is avoided since only air would be drawn in if the valve member 36 failed. Also the hemodialysis machine 10 preferably includes sensors on the pairs of connections 56, 40; 70, 32 and 92, 34 such that the hemodialysis machine 10 will not operate in a requested mode if the proper connectors are not in the proper locations, as will be further discussed with respect to FIG. 4.

Further, it is preferable that an air buffer be maintained between fluids and hence the chemical control valve 26 is energized first. This ensures that air will be drawn into the line 68 before any chemical. The air provides a fluid flushing action to remove the prior fluid, before a new fluid is entered into the hemodialysis machine 10.

The valve 78 also forms a portion of the chemical treatment system, since in its normally open position all the fluid from the pump 66 flows into the line 80. This often is sufficient, since the operator may only wish to chemically treat the A/B and downstream portions of the hemodialysis machine 10, since these portions are the most susceptible to infection potential and most likely to be in need of chemical treatment.

The valve 78, however, can be energized to provide a full system chemical treatment. In this case the line 80 is closed and the chemical is fed through the valve 78 via a line 100 through the heat exchanger 18 and via the line 22 to the water conditioning unit 20 and to the W/A portion of the hemodialysis machine 10.

The properly diluted chemical is fed through the water conditioning unit 20 and both lines 24 and 42. The line 24 feeds the chemical solution through the inlet 28 and the outlet 30 to the now open W/A rinse port 40. Only a small portion is metered through the line 54, with the remaining flow joining with the flow from the line 42 to flow into the line 44. None of the chemical solution is drawn into the valve 26 from the inlet 28, since the body of the valve 26 is closed by the valve member 36. The W/A pump 50 is operated at a fixed speed that meters approximately 28 ml/min of chemical solution from the port 40. The A/B pump 66 pumps the required volume of the chemical concentrate to obtain the proportioning ratio applicable to the particular chemical. Typically, this ranges from 20.13× (19.13 parts water plus 1 part chemical) to 100× (99 parts water plus part chemical). A flow rate is selected of 500 ml/min, which is controlled by the dialysate monitor in control unit 84. This flow rate is maintained for all chemicals except Renalin which must be diluted at 100×. To accomplish this dilution, the flow rate is set for 800 ml/min and the A/B pump 66 is set to pump at or close to its lowest operating range at 8 ml/min. This allows the hemodialysis machine 10 to be chemically sterilized by utilizing a one percent concentration of Renalin. Renalin is a cold sterilant for dialysis use which is placed into the source 90. The Renalin solution is allowed to dwell in the hemodialysis machine 10 for a minimum of eleven (11) hours. Pre-dilution of Renalin is impractical, because this results in a reduced shelf life on the order of seven (7) days.

The chemical treatment of the hemodialysis machine 10 involve three (3) or four (4) cycles depending upon the treatment chemicals employed. Some, such as bleach, are introduced into the hemodialysis machine with an exposure time only equal to when the chemical is present. Formaldehyde requires a two (2) hour minimum dwell period after it is introduced into the hemodialysis machine 10. Typically, Formaldehyde is allowed to dwell in the hemodialysis machine 10 overnight or over a weekend. A post rinse is performed when the hemodialysis machine 10 is restarted. The chemical Actril requires a thirty (30) minute dwell period. Where a long overnight dwell time is desired or required, the operator can control the time by turning the hemodialysis machine 10 off and then back on. For short dwell times on the order of minutes, the hemodialysis machine 10 can define the dwell period. The hemodialysis machine 10 utilizes more power in the system defined dwell period and thus the operator may prefer to turn the hemodialysis machine 10 off to consume less power. The hemodialysis machine 10 retains the fact that it is in a dwell state.

Typical chemical treatment cycles are as follows:

(1) Pre-rinse: A water only rinse (illustrated in FIG. 2) initiated when all three ports (32, 40 and 92) are engaged. The hemodialysis machine 10 will not operate in the rinse mode without the port 40 being connected. If the chemical port 34 is not connected then the hemodialysis machine 10 assumes that a manual chemical treatment is to take place under operator control. If the connector 92 is engaged in the chemical port 34, then the chemical code will be verified and accepted. At that point the hemodialysis machine 10 requires both of the rinse connectors 56 and 70 to be engaged in the respective ports 40 and 32.

(2) Chemical Intake: Some chemicals are drawn in rapidly for about two (2) minutes and then reduced to the required dilution ratio. Chemicals requiring no dwell period are processed for a sufficient time to ensure adequate exposure.

(3) Dwell Period: This is a period of minutes defined by the hemodialysis machine 10 with automatic cycling to post rinse or operator defined longer dwell periods, such as overnight.

(4) Post Rinse: This is a required period of water rinse (FIG. 2) that helps ensure that the chemical has been removed from the hemodialysis machine 10. This preferably occurs at the highest flow rate, for example, 800 ml/min, to minimize the post rinse time period.

When the chemical intake potion of the chemical treatment cycle is completed, the vent valve 98 is preferably first opened for a short time period, on the order of four (4) seconds, then the chemical control valve 26 is deenergized. This removes residual chemical from the chemical control valve 26 and also places a bubble of air between the chemical and the rinse water which follows the chemical treatment cycle. The vent valve 98, being opened allows residual chemical fluid to drain back into the container 90. Thus, when the operator disconnects the container 90, spillage resulting in handling hazard and odor is minimized.

The hemodialysis machine 10 also can be operated in either the acetate or bicarbonate dialysis modes. The bicarbonate dialysis mode was described above. The acetate mode, though similar, is a combination of the modes illustrated in FIGS. 1 and 2. The concentrate solution 64 now is acetate the concentrate solution 52 is now eliminated and the pump 50 is connected only to the port 40, as illustrated in the rinse mode of FIG. 2.

Although a specific three way valve structure 26 has been illustrated, the invention can be practiced with other types of valving including a plurality of valves providing the same valving functions as the chemical control valve 26. The chemical treatment system includes as its primary elements the valves 26, 78 and 98 which operate to connect the hemodialysis machine 10 for operation in the rinse and chemical treatment modes.

The flow sensor 74 is utilized with the A/B pump 66, since the pump 66 can be required to pump at very low rates. The flow sensor 74 ensures that the chemical source 90 is not empty and also helps to ensure the adequacy of the dialysis operation.

Figure 4:
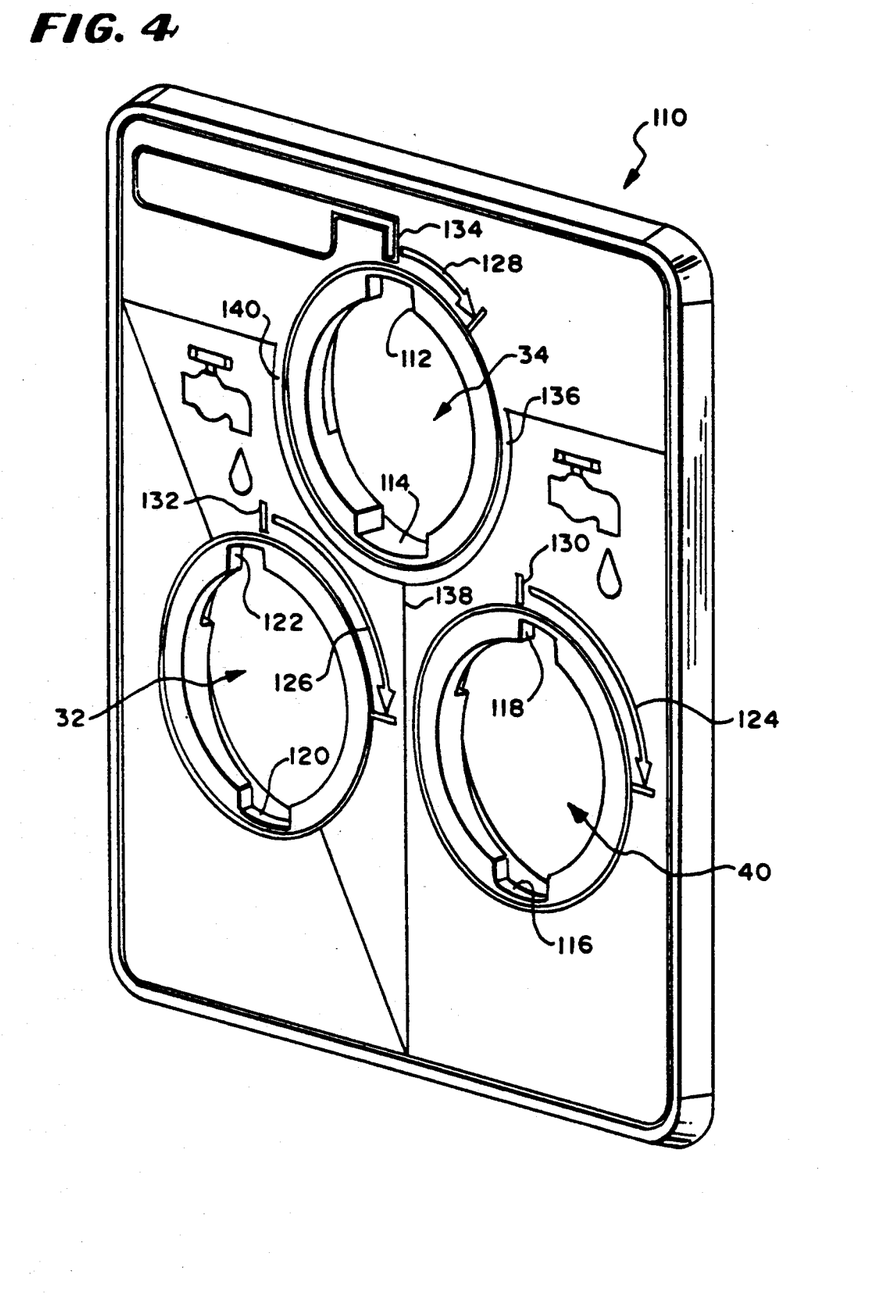
FIG. 4 is a partial perspective view of one embodiment of a multi-assembly port of the present invention.

A multi-port safety assembly 110 is illustrated in FIG. 4. The connectors 56, 70 and 92 are configured (not illustrated) to fit only into their respective ports 40, 32 and 34 physically defined by the assembly 110. The connectors 56, 70 and 92 each include tabs which allow them only to fit into their respective port configuration.

The chemical port 34 includes a tab slot 112 at a twelve o'clock position and a second tab slot 114 at a six o'clock position. The W/A port 40 also includes a tab slot 116 at the six o'clock position and a tab slot 118 offset from the twelve o'clock position toward the one o'clock position. The A/B port 32 includes a tab slot 120 at the six o'clock position like the tab slot 116, but the tab slots 116 and 120 are more narrow than the tab slot 114. The port 32 further includes a tab slot 122, but the tab slot 122 is offset from the twelve o'clock position toward the eleven o'clock position.

Thus, the respective connectors 56, 70 and 92 cannot physically be inserted into the wrong port. Further, as previously stated, the connector 92 preferably is a female connector, while the connectors 56 and 70 are male connectors. This adds another level of safety to prevent the insertion of the chemical treatment connector 92 in any port other than the port 34.

The connectors 56, 70 and 92 are inserted into their respective ports and then rotated in a camming configuration to a fully engaged position as shown by respective arrows 124, 126 and 128. The connectors 56 and 70 also include a magnet (not illustrated) which in the fully engaged position aligns with a hall effect switch located respectively at locations 130 and 132 adjacent the ports 40 and 32. Thus the hemodialysis machine 10 can confirm that the connectors 56 and 70 are connected in their respective fully engaged positions.

The chemical treatment port 34 includes four hall effect switches located at four locations 134, 136, 138 and 140 respectively (indicated by the characters A, B, C and D in Table I). The connector 92 includes a pair of magnets. The hemodialysis machine 10 cannot validate a chemical unless two hall effect switch positions are pulled low (LO) by an adjacent magnet in the connector 92. The undefined position is an operator defined position in which the operator can input the chemical, dwell and post rinse operations of the hemodialysis machine 10 cycle.

TABLE I

| CHEMICAL | MAGNET POSITION | CHEMICAL TREATMENT CODES | | | |
|---|---|---|---|---|---|
| | | A | B | C | D |
| Formaldehyde | B-C | HI | LO | LO | HI |
| Bleach 5% | A-D | LO | HI | HI | LO |
| Vinegar | C-D | HI | HI | LO | LO |
| Actril | A-B | LO | LO | HI | HI |
| Renalin | A-C | LO | HI | LO | HI |
| Undefined | B-D | HI | LO | HI | LO |

Another hall effect switch feature of the hemodialysis machine 10, which is important in each of the dialysis, chemical treatment and rinsing modes is the minimization of stagnation. The connections of the ports 32, 34 and 40 to their respective locations are kept very short. The valve 26 has continuous fluid flow through the inlet 28 and the outlet 30 to prevent stagnation in the valve 26 or the lines 24 and 38. A possible source of stagnation is the line 80, when the hemodialysis machine 10 is switched to a full chemical treatment through the valve 78 and the line 100. The line 100 as well as other lines which do not always have a fluid flow are kept to a minimum length. To prevent any residual in the line 80, at the end of the post rinse cycle, the valve 78 switches back to rinse the line 80 before the post rinse cycle is terminated.

A further safety feature of the hemodialysis machine 10 is the safe guard against negative pressure being introduced into the hemodialysis machine 10, which potentially could draw in chemical from the port 34. The water conditioning unit 20 includes a pressure switch which will turn the hemodialysis machine 10 off if the water pressure is too low. The valve 26 has the port 34 normally closed off by the valve member 36. The vent valve 98 has the port 34 exposed to air. Lastly, the hemodialysis machine 10 will not operate in a dialysis mode if the hall effect switch for the port 34 indicates that the connector 92 is engaged. Thus the hemodialysis machine 10 includes four negative pressure safeguards to prevent the accidental introduction of a treatment chemical.

We claim as our invention:

1. In a hemodialysis machine having a source of water, a pair of proportioning pumps each having inlet means adapted to be connected to said source and outlet means adapted to be coupled to a dialyzer, the improvement comprising:
   a chemical treatment system including first valve means for coupling the inlet means of each of said proportioning pumps to said source of water by flow paths not containing the other pump for rinsing the hemodialysis machine in a rinse mode and second valve means for decoupling at least a first one of said proportioning pumps from said source of water and to a source of chemical for chemically treating at least a portion of said hemodialysis machine in a chemical treatment mode and including third valve means for coupling the outlet means of said first one of said proportioning pumps to the inlet means of said second one of said proportioning pumps in the chemical treatment mode for chemically treating substantially all of said hemodialysis machine.

2. The improvement as defined in claim 1 including flow sensing means coupled to said first one of said proportioning pumps to ensure that said source of chemical is not empty.

3. The improvement as defined in claim 1 including vent valve means for decoupling said source of chemical and coupling a source of air to said inlet means of said first one of said proportioning pumps.

4. The improvement as defined in claim 3 wherein said second valve means includes means for decoupling said source of air and coupling said source of water to said inlet means of said first one of said proportioning pumps.

5. The improvement as defined in claim 3 including a single three way control valve forming said first and second valve means.

6. The improvement as defined in claim 5 wherein said control valve includes a first port for coupling the inlet means of a second one of said proportioning pumps to said source of water in said rinse and chemical treatment modes, said first port also coupling said inlet means of said first one of said proportioning pumps to said source of water in said rinse mode and a second port for coupling said inlet means of said first one of said proportioning pumps to said source of chemical in said chemical treatment mode.

7. The improvement as defined in claim 6 wherein said control valve includes a valve member normally in said rinse mode positioned to block said second port and in an energized position forming said chemical treatment mode positioned to block said first port.

8. The improvement as defined in claim 7 including vent valve means for decoupling said source of chemical and coupling a source of air to said inlet means of said first one of said proportioning pumps.

9. The improvement as defined in claim 8 wherein said vent valve means include means for decoupling said source of air and coupling said source of water to said inlet means of said first one of said proportioning pumps.

10. In a hemodialysis machine having a source of water, a pair of proportioning pumps each having inlet mean adapted to be connected to said source and outlet means adapted to be coupled to a dialyzer, the improvement comprising:

a chemical treatment system including first valve means for coupling the inlet means of both of said proportioning pumps to said source of water for rinsing the hemodialysis machine in a rinse mode and second valve means for decoupling at least a first one of said proportioning pumps from said source of water and to a source of chemical for chemically treating at least a portion of said hemodialysis machine in a chemical treatment mode and including vent valve means for decoupling said source of chemical and coupling a source of air to said inlet means of said at least first one of said proportioning pumps.

11. The improvement as defined in claim 10 including third valve means for coupling the outlet means of said at least first one of said proportioning pumps to the inlet means of said second one of said proportioning pumps in the chemical treatment mode for chemically treating all of said hemodialysis machine.

12. The improvement as defined in claim 10 wherein said second valve means include means for decoupling said source of air and coupling said source of water to said inlet means of said at least first one of said proportioning pumps.

13. The improvement as defined in claim 10 including a single three way control valve forming said first and second valve means.

14. The improvement as defined in claim 13 wherein said control valve includes a first port for coupling the inlet means of a second one of said proportioning pumps to said source of water in said rinse and chemical treatment modes, said first port also coupling said inlet means of said at least first one of said proportioning pumps to said source of water in said rinse mode and a second port for coupling said inlet means of said at least first one of said proportioning pumps to said source of chemical in said chemical treatment mode.

15. The improvement as defined in claim 14 wherein said control valve includes a valve member normally in said rinse mode positioned to block said second port and in an energized position forming said chemical treatment mode positioned to block said first port.

16. The improvement as defined in claim 15 including vent valve means for decoupling said source of chemical and coupling a source of air to said inlet means of said first one of said proportioning pumps.

17. The improvement as defined in claim 16 wherein said vent valve means includes means for decoupling said source of air and coupling said source of water to said inlet means of said at least first one of said proportioning pumps.

18. In a hemodialysis machine having a source of water, a pair of proportioning pumps each having inlet mean adapted to be connected to said source and outlet means adapted to be coupled to a dialyzer, the improvement comprising:

a chemical treatment system including first valve means for coupling the inlet means of each of said proportioning pumps to said source of water by flow paths not containing the other pump for rinsing the hemodialysis machine in a rinse mode and second valve means for decoupling at least a first one of said proportioning pumps from said source of water and to a source of chemical for chemically treating at least a portion of said hemodialysis machine in a chemical treatment mode and including a single three way control valve forming said first and second valve means.

19. The improvement as defined in claim 18 including third valve means for coupling the outlet means of said at least first one of said proportioning pumps to the inlet means of said second one of said proportioning pumps in the chemical treatment mode for chemically treating all of said hemodialysis machine.

20. The improvement as defined in claim 18 including vent valve means for decoupling said source of chemical and coupling a source of air to said inlet means to said at least first one of said proportioning pumps.

21. The improvement as defined in claim 20 wherein said second valve means include means for decoupling said source of air and coupling said source of water to said inlet means of said at least first one of said proportioning pumps.

22. The improvement as defined in claim 18 wherein said control valve includes a first port for coupling the inlet means of a second one of said proportioning pumps to said source of water in said rinse and chemical treatment modes, said first port also coupling said inlet means of said at least first one of said proportioning pumps to said source of water in said rinse mode and a second port for coupling said inlet means of said at least first one of said proportioning pumps to said source of chemical in said chemical treatment mode.

23. The improvement as defined in claim 22 wherein said control valve includes a valve member normally in said rinse mode positioned to block said second port and in an energized position forming said chemical treatment mode positioned to block said first port.

24. The improvement as defined in claim 23 including vent valve means for decoupling said source of chemical and coupling a source of air to said inlet means of said at least first one of said proportioning pumps.

25. The improvement as defined in claim 24 wherein said vent valve means include means for decoupling said source of air and coupling said source of water to said inlet means of said at least first one of said proportioning pumps.

26. An improved hemodialysis machine adapted to be connected to a source of water, comprising:
a chemical control valve having an inlet port adapted for coupling to the source of water, a first outlet port coupled to dialzying means and adapted to be coupled to the inlet of a first proportioning pump, a second outlet port coupled to said inlet port in a first valve position and to a chemical inlet port in a second valve position, said second outlet port also coupled to the inlet of a second proportioning pump;
both said proportioning pumps having outlet means coupled to said dialyzing means, including valve means for coupling said outlet means of said second proportioning pump to said inlet of said first proportioning pump for chemically treating substantially all of said hemodialysis machine.

27. The hemodialysis machine as defined in claim 26 including flow sensing means coupled to said second one of said proportioning pumps to ensure that said source of chemical is not empty.

28. The hemodialysis machine as defined in claim 26 including vent valve means for decoupling said chemical inlet port and coupling an inlet port to said inlet of said second proportioning pumps.

29. The hemodialysis machine as defined in claim 25 wherein said control valve is a single three way control valve.

30. The hemodialysis machine as defined in claim 29 wherein said control valve includes a valving member normally non-energized forming said first valve position blocking said chemical inlet port and having an energized position blocking said inlet port and coupling said second outlet port to said chemical inlet port.

31. The hemodialysis machine as defined in claim 30 including vent valve means for decoupling said chemical inlet port by coupling a source of air to said second outlet port.

32. The hemodialysis machine as defined in claim 31 including said vent valve means having a normally open position coupling said source of air to said chemical inlet port and said control valve.

33. The hemodialysis machine as defined in claim 26 including said first and second outlet ports and said chemical inlet ports formed in a safety assembly acquiring physically different connectors for each of said inlet and outlet ports.

34. The hemodialysis machine as defined in claim 33 including means for sensing which of said connectors are engaged in which of said inlet and outlet ports.

35. The hemodialysis machine as defined in claim 34 including multi-position sensing means for sensing which and whether ones of said connectors are connected to said chemical inlet port.

36. The hemodialysis machine as defined in claim 34 wherein said sensing means include magnetic effect sensing.

37. The hemodialysis machine as defined in claim 34 including multi-position sensing means for sensing which of said connectors is connected to said chemical inlet port.

38. An improved hemodialysis machine adapted to be connected to a source of water, comprising:
a chemical control valve having an inlet port adapted for coupling to the source of water, a first outlet port coupled to dialzying means and adapted to be coupled to the inlet of a first proportioning pump, a second outlet port coupled to said inlet port in a first valve position and to a chemical inlet port in a second valve position, said second outlet port also coupled to the inlet of a second proportioning pump;
both said proportioning pumps having outlet means coupled to said dialyzing means; and
vent valve means for decoupling said chemical inlet port and coupling an air inlet port from a source of air to said inlet of said second proportioning pump.

39. The hemodialysis machine as defined in claim 38 including valve means for coupling said outlet means of said second proportioning pump to said inlet of said first proportioning pump for chemically treating substantially all of said hemodialysis machine.

40. The hemodialysis machine as defined in claim 38 wherein said control valve is a single three way control valve.

41. The hemodialysis machine as defined in claim 40 wherein said control valve includes a valving member normally non-energized forming said first valve position blocking said chemical inlet port and having an energized position blocking said inlet port and coupling said second outlet port to said chemical inlet port.

42. The hemodialysis machine as defined in claim 41 including vent valve means for decoupling said chemical inlet port by coupling a source of air to said second outlet port.

43. The hemodialysis machine as defined in claim 42 including said vent valve means having a normally open position coupling said source of air to said chemical inlet port and said control valve.

44. The hemodialysis machine as defined in claim 38 including said first and second outlet ports and said chemical inlet port formed in a safety assembly acquiring physically different connectors for each of said inlet and outlet ports.

45. The hemodialysis machine as defined in claim 44 including means for sensing which of said connectors are engaged in which of said inlet and outlet ports.

46. The hemodialysis machine as defined in claim 45 including multi-position sensing means for sensing which of said connectors is connected to said chemical inlet port.

47. The hemodialysis machine as defined in claim 45 wherein said sensing means include magnetic effect sensing.

48. An improved hemodialysis machine adapted to be connected to a source of water, comprising:
a chemical control valve having an inlet port adapted for coupling to the source of water, a first outlet port coupled to dialzying means and adapted to be coupled to the inlet of a first proportioning pump, a second outlet port coupled to said inlet port in a first valve position and to a chemical inlet port in a second valve position, said second outlet port also coupled to the inlet of a second proportioning pump;

both said proportioning pumps having outlet means coupled to said dialyzing means; and said control valve is a single three way control valve including a valving member normally non-energized forming said first valve position blocking said chemical inlet port and having an energized position blocking said inlet port and coupling said second outlet port to said chemical inlet port.

49. The hemodialysis machine as defined in claim 48 including vent valve means for decoupling said chemical inlet port by coupling a source of air to said second outlet port.

50. The hemodialysis machine as defined in claim 49 including vent valve means having a normally open position coupling said source of air to said chemical inlet port and said control valve.

51. An improved hemodialysis machine adapted to be connected to a source of water, comprising:

a chemical control valve having an inlet port adapted for coupling to the source of water, a first outlet port coupled to dialzying means and adapted to be coupled to the inlet of a first proportioning pump, a second outlet port coupled to said inlet port in a first valve position and to a chemical inlet port in a second valve position, said second outlet port also coupled to the inlet of a second proportioning pump;

both said proportioning pumps having outlet means coupled to said dialyzing means; and including said first and second outlet ports and said chemical inlet port formed in a safety assembly requiring physically different connectors for each of said inlet and outlet ports.

52. The hemodialysis machine as defined in claim 51 including means for sensing which of said connectors are engaged in which of said inlet and outlet ports.

53. The hemodialysis machine as defined in claim 52 including multi-position sensing means for sensing which of said connectors is connected to said chemical inlet port.

54. The hemodialysis machine as defined in claim 52 wherein said sensing means include magnetic effect sensing.

* * * * *